(12) United States Patent
Martens

(10) Patent No.: US 9,572,987 B2
(45) Date of Patent: *Feb. 21, 2017

(54) MULTI-ELECTRODE NEUROSTIMULATION DEVICE

(71) Applicant: Medtronic Bakken Research Center B.V., Maastricht (NL)

(72) Inventor: Hubert Cecile François Martens, Eindhoven (NL)

(73) Assignee: Medtronic Bakken Research Center B.V., Maastricht (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/696,136

(22) Filed: Apr. 24, 2015

(65) Prior Publication Data

US 2015/0224316 A1 Aug. 13, 2015

Related U.S. Application Data

(63) Continuation of application No. 13/285,084, filed on Oct. 31, 2011, now Pat. No. 9,020,604.

(30) Foreign Application Priority Data

Oct. 29, 2010 (EP) .................................. 10189489

(51) Int. Cl.
*A61N 1/36* (2006.01)
*A61N 1/05* (2006.01)

(52) U.S. Cl.
CPC ......... *A61N 1/36139* (2013.01); *A61N 1/0531* (2013.01); *A61N 1/0553* (2013.01);
(Continued)

(58) Field of Classification Search
CPC ............ A61N 1/36182; A61N 1/36146; A61N 1/36139; A61N 1/36157; A61N 1/36185
See application file for complete search history.

(56) References Cited

U.S. PATENT DOCUMENTS 4,019,518 A 4/1977 Maurer et al.
7,442,183 B2 10/2008 Baudino et al.
(Continued)

FOREIGN PATENT DOCUMENTS

WO 2010065888 A1 6/2010
WO 2010120823 A1 10/2010

OTHER PUBLICATIONS

Official Communication issued by the European Patent Office dated Jan. 31, 2014, for European Patent Application No. 11779379.4.
(Continued)

*Primary Examiner* — Kennedy Schaetzle
(74) *Attorney, Agent, or Firm* — Shumaker & Sieffert, P.A.

(57) ABSTRACT

A neurostimulation device is provided comprising an input, a neurostimulation probe, a stimulation unit and a distribution calculation module. At the input stimulation data is received comprising information relating to a stimulation preferability and an orientation of at least one fiber bundle. The neurostimulation probe comprises an array of stimulation electrodes which are coupled to the stimulation unit. The stimulation unit, in accordance with a specified current distribution, provides currents to the respective stimulation electrodes for generating an electric field gradient. The distribution calculation module is coupled to the input and the stimulation unit for based on the stimulation data determining a preferred position and orientation for the electric field gradient, and based on the preferred position and orientation for the electric field gradient, calculating the specified current distribution.

20 Claims, 3 Drawing Sheets

(52) U.S. Cl.
CPC ..... *A61N 1/36146* (2013.01); *A61N 1/36157* (2013.01); *A61N 1/36182* (2013.01); *A61N 1/36185* (2013.01)

(56) References Cited

U.S. PATENT DOCUMENTS

| | | | |
|---|---|---|---|
| 7,881,805 B2 | 2/2011 | Bradley et al. | |
| 8,239,038 B2 | 8/2012 | Wolf | |
| 9,020,604 B2* | 4/2015 | Martens | A61N 1/0531 607/45 |
| 2003/0055466 A1 | 3/2003 | Ben-Haim et al. | |
| 2005/0070982 A1 | 3/2005 | Heruth et al. | |
| 2006/0017749 A1 | 1/2006 | McIntyre et al. | |
| 2006/0253182 A1 | 11/2006 | King | |
| 2008/0215125 A1 | 9/2008 | Farah et al. | |
| 2008/0294211 A1* | 11/2008 | Moffitt | A61N 1/0553 607/9 |
| 2009/0287271 A1 | 11/2009 | Blum et al. | |
| 2010/0030298 A1 | 2/2010 | Martens et al. | |
| 2011/0077717 A1 | 3/2011 | Poletto | |

OTHER PUBLICATIONS

Butson, C.R., et al., "Role of electrode design on the volume of tissue activated during deep brain stimulation," Journal of Neural Engineering, vol. 3, No. 1, Mar. 1, 2006, 8 pp. Butson, C.R., et al., "StimExplorer: deep brain stimulation parameter selection software system," Acta NeuroChir. Suppl., Jan. 1, 2007, vol. 97, pp. 569-574.
Butson, C.R., et al., "StimExplorer: deep brain stimulation parameter selection software system," Acta NeuroChir. Suppl., Jan. 1, 2007, vol. 97, pp. 569-574.
International Search Report and Written Opinion from International Application No. PCT/EP2011/069090, dated Mar. 7, 2012, 13 pp.
International Preliminary Report on Patentability from International Application No. PCT/EP2011/069090, dated Apr. 30, 2013, 9 pp.
Prosecution History from U.S. Appl. No. 13/285,084, dated Dec. 19, 2012 through Jan. 28, 2015, 29 pp.
Reply to Official Communication issued by the European Patent Office dated Jan. 31, 2014, for European Patent Application No. 11779379.4, filed Aug. 11, 2014, 26 pages.

\* cited by examiner

MULTI-ELECTRODE NEUROSTIMULATION DEVICE

CROSS-REFERENCE TO RELATED APPLICATIONS

This application is a continuation of U.S. application Ser. No. 13/285,084, which was filed on Oct. 31, 2011, now U.S. Pat. No. 9,020,604, and claims the benefit of European Patent Application No. 10 189 489.7 filed Oct. 29, 2010, each of which is incorporated by reference herein in its entirety.

FIELD OF THE INVENTION

This invention relates to a neurostimulation device comprising an input for receiving stimulation data comprising information relating to a stimulation preferability and an orientation of at least one fiber bundle, a neurostimulation probe with an array of stimulation electrodes, a stimulation unit coupled to the stimulation electrodes for, in accordance with a specified current distribution, providing currents to the respective stimulation electrodes for generating an electric field and a distribution calculation module coupled to the input and the stimulation unit for based on the stimulation data determining a preferred position for the electric field and based on the preferred position for the electric field calculating the specified current distribution.

BACKGROUND OF THE INVENTION

Systems for providing neurostimulation via an implanted probe are used for treatment of disorders such as chronic pain, Parkinson's disease, tremor and dystonia. Neurostimulation is used for stimulating neural tissue in the brain, the spinal cord and peripheral nerves. In the following, neurostimulation of brain tissue will be discussed. However, the system and method according to the invention can also be used for neurostimulation of, e.g., the spinal cord and peripheral nerves. The probe is surgically implanted in the brain, close to the brain tissue that is to be stimulated. When using neurostimulation it is important to stimulate the tissue that needs stimulation and to avoid stimulation of other nearby tissue. Correct placement of the probe thus is an important step in a successful neurostimulation treatment. In known systems for planning implantation of the probe, imaging techniques such as Magnetic Resonance Imaging (MRI) are used to visualize the target region. The surgeon tries to locate the structures that need stimulation and tries to define a surgical plan to implant the probe in the identified structure.

A known way of trying to stimulate the correct tissue region is to implant a probe with a plurality of electrodes and to select only a subset of these electrodes so as to stimulate only specific tissue regions. This is, e.g., described in U.S. patent applications US 2008/0215125 and U.S. 2010/0030298. These U.S. applications describe a probe with a plurality of electrodes which is implanted close to the region of interest. Electrical charges are supplied to a subset of these electrodes to selectively stimulate specific tissue regions. Also in U.S. Pat. No. 7,442,183 a subset of a plurality of electrodes is activated to steer an electrical field to the target region. In U.S. Pat. No. 7,442,183, it is noted that the selective activation of a subset of the electrodes makes the precise probe location relative to the target structure less critical.

Although the use of electrode arrays does enable steering 3D electric field distributions to specific tissue regions, the full range of 3D stimulation patterns that can be created is still dependent on the exact position and orientation of the probe. For optimal therapy delivery options and tuning flexibility thereof an optimal lead positioning should be arranged in the therapy planning phase.

OBJECT OF THE INVENTION

It is an object of the invention to provide a neurostimulation device allowing for more accurate targeting of specific neurological structures in order to improve the neurostimulation treatment.

BRIEF SUMMARY OF THE INVENTION

According to a first aspect of the invention, this object is achieved by providing neurostimulation device comprising an input, a neurostimulation probe, a stimulation unit and a distribution calculation module. At the input stimulation data is received comprising information relating to a stimulation preferability and an orientation of at least one fiber bundle. The neurostimulation probe comprises an array of stimulation electrodes which are coupled to the stimulation unit. The stimulation unit, in accordance with a specified current distribution, provides currents to the respective stimulation electrodes for generating an electric field gradient. The distribution calculation module is coupled to the input and the stimulation unit for based on the stimulation data determining a preferred position and orientation for the electric field gradient, and based on the preferred position and orientation for the electric field gradient, calculating the specified current distribution.

The neurostimulation device according to the invention does not only take into account the position of the target structure but also its orientation when applying a stimulation field. Especially for fiber bundles, the orientation of the electric stimulation field relative to the orientation of the fiber bundle is an important factor determining the effectiveness of the neurostimulation therapy. While the prior art neurostimulation devices only try to stimulate the brain at specific target positions, the neurostimulation device according to the invention also takes into account the direction of the target fibers and the direction of the gradients of the electric stimulation fields that are generated.

It has been found that activation of certain fibers is most easily achieved when the electric field gradient is parallel or approximately parallel to the targeted fiber bundle. Selective non-activation of the fibers is most easily achieved with an electric field gradient that is perpendicular or approximately perpendicular to the non-targeted fiber bundle. Using state of the art imaging techniques, such as Diffusion Tensor Imaging (DTI), it is possible to identify individual fiber bundles and their positions and orientations. The distribution calculation module uses this information to determine a position and orientation of the optimal electrical field gradient for the neurostimulation therapy. This optimal electrical field gradient may result in a maximum stimulation of the target fiber, but may also provide a balance between stimulating targets that need stimulation and avoiding stimulation of structures that are preferably not stimulated. When the optimal electrical field gradient is known, a distribution of stimulation currents over the electrodes in the array is calculated for obtaining the optimal electrical field gradient. The thus obtained distribution of stimulation currents is then provided to the stimulation unit.

The stimulation unit applies the calculated currents to the respective electrodes in the array to obtain the optimal electrical field gradient. The neurostimulation device according to the invention thus makes it possible to generate electric stimulation fields with field gradients that are (approximately) parallel to fiber bundles that should be stimulated and/or (approximately) perpendicular to fiber bundles that should not be stimulated.

When, e.g., a particular fiber bundle or section of a fiber bundle is selected for stimulation, the orientation of the target fibers is compared to the relative position and orientation of the electrode array. This portion of the target fiber tract may then be projected onto the stimulation array, resulting in an orientation vector. In an embodiment of the neurostimulation device according to the invention, three groups of electrodes are then activated to generate an electrical field with a gradient parallel to the orientation vector. In this example, the specified current distribution is a tripolar stimulation profile. A first group of electrodes with a first polarity is located centrally on the orientation vector. A second and third group of electrodes are selected at opposite sides of the first group and along the orientation vector. The second and third group have a polarity opposite from the first group. The total current may be balanced by providing equal currents to the second and third group of electrodes, the first group of electrodes receiving a double current with opposite polarity.

The stimulation data may further comprise information relating to the fiber diameter at different sections of the fiber bundle. When the fiber bundle is small, it is easier to focus an electrical field on the fiber bundle without inadvertently stimulating other nearby tissue. Furthermore, the electrical field strength that is needed for an effective stimulation therapy is smaller. When using such diameter data, stimulation electrodes may be selected for generating an electrical field gradient close to or right at the narrower sections of the fiber bundle.

The stimulation data may further comprise information relating to fiber orientation variations over the length of the fiber bundle. For example, when trying to stimulate multiple fiber bundles or when trying to avoid stimulation of a nearby fiber bundle, it may be better to stimulate a differently oriented section of the fiber bundle instead of the narrowest section or the section closest to the stimulation electrodes.

Thus, in a preferred embodiment of the neurostimulation device according to the invention, a current distribution is specified which results in an optimal balance between maximizing therapeutic effect and minimizing adverse side effects. This optimal current distribution takes into account diameters and orientations of different sections of one or more targeted fiber bundles and of one or more fiber bundles for which stimulation is preferably avoided.

According to a second aspect of the invention, a method calculating a specified current distribution for an array of stimulation electrodes of a neurostimulation device is provided. The method comprises the steps of receiving stimulation data comprising information relating to a stimulation preferability and an orientation of at least one fiber bundle, based on the stimulation data determining a preferred position and orientation for an electric field gradient to be generated by the array of stimulation electrodes, and based on the preferred position and orientation for the electric field gradient, calculating the specified current distribution. The specified current distribution may then be applied to the stimulation electrodes for generating the electric field gradient and therewith providing the neurostimulation therapy.

According to a further aspect of the invention, a computer program product is provided for causing a processor to perform the above described method. These and other aspects of the invention are apparent from and will be elucidated with reference to the embodiments described hereinafter.

DETAILED DESCRIPTION OF THE INVENTION

Figure 1:
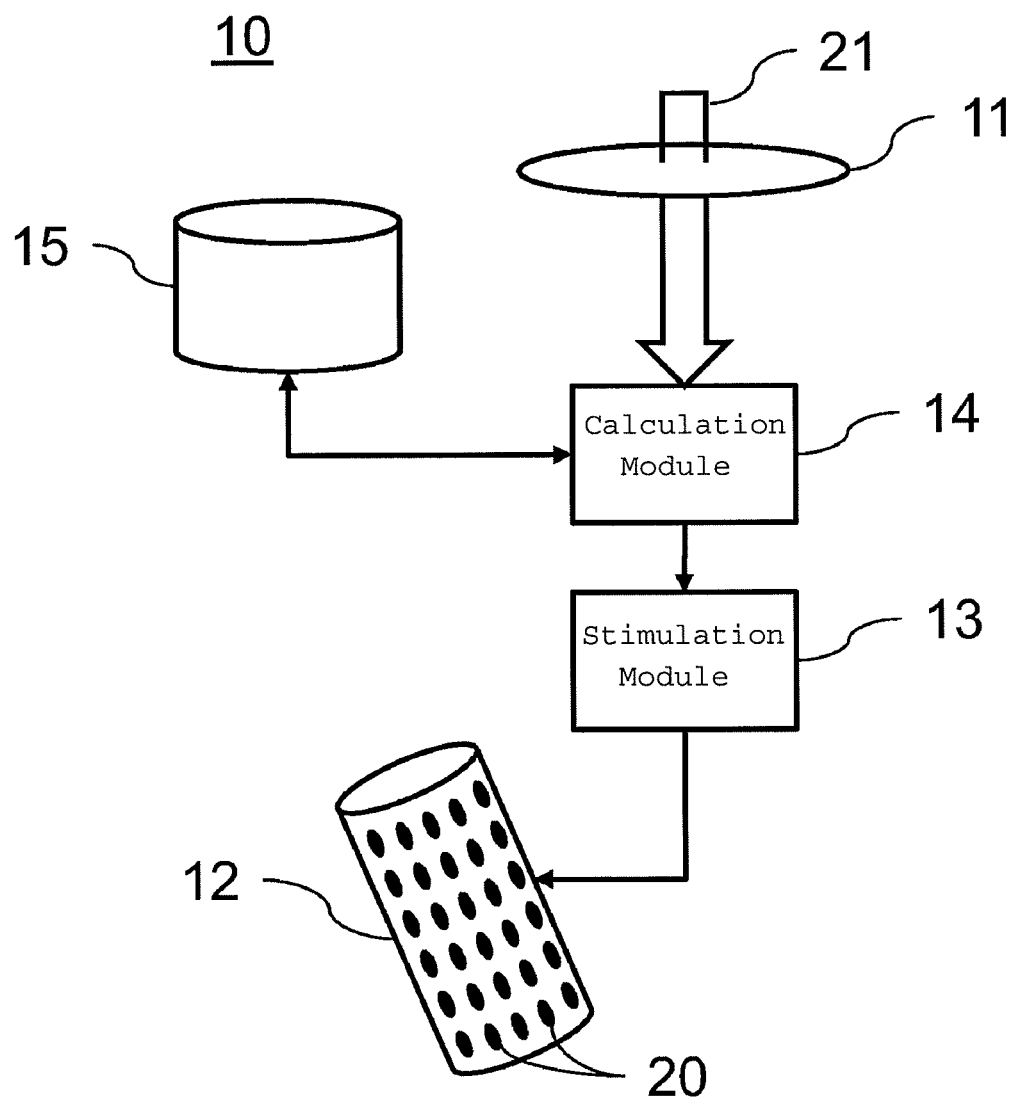
FIG. 1 schematically shows a neurostimulation device according to the invention.

FIG. 1 schematically shows a neurostimulation device 10 according to the invention. The neurostimulation device 10 comprises a neurostimulation probe 12 with an array of stimulation electrodes 20. When the probe 12 is implanted in a patient's brain, the stimulation electrodes 20 can provide neurostimulation therapy to nearby neurological tissue by generating electrical fields. A stimulation unit 13 provides electrical currents to the electrodes 20 for generating the electrical field. By sending different currents to selected electrodes 20, the electrical field can be targeted at specific tissue regions close to the probe 12. According to the invention, the stimulation module 13 receives a specified current distribution from distribution calculation module 14. The specified current distribution specifies what current should be applied to which electrode 20. The calculation of the specified current distribution is based on data 21 describing the fiber bundle that should or 20 should not be stimulated and will be discussed below with reference to FIG. 2. The data 21 needed for calculating the specified current distribution is received at an input 11 of the device. This data 21 may be received through wired and/or wireless communication with a system for planning the neurostimulation therapy. The received data may be stored in a memory 15 of the device 10 for enabling use of the device 10 when the planning system is not available.

The data 21 comprises information about the stimulation preferability of selected fiber bundles close to the position where the probe is implanted. The stimulation preferability may be a binary value indicating 'stimulation' or 'no stimulation', but may also be a continuous or discrete value on a scale ranging from 'stimulation highly preferable' to 'absolutely no stimulation'. The data 21 also comprises information describing the position and orientation of the selected fibers relative to the position and orientation of the probe 12. Such information is needed for determining the strength and direction of the electric stimulation field that is to be generated by the stimulation unit 13 and the stimulation electrodes 20. Additionally, the data 21 may comprise information about electric properties of the tissue close to the probe 12. The electrical properties of the nearby tissue influence the relation between the applied stimulation currents and the thereby generated electrical field.

The data 21 may further comprise information relating to the fiber diameter at different sections of the fiber bundle. When the fiber bundle is small, it is easier to focus an electrical field on the fiber bundle without inadvertently stimulating other nearby tissue. Furthermore, the electrical field strength that is needed for an effective stimulation therapy is smaller. When using such diameter data, stimulation electrodes 20 may be selected for generating an electrical field gradient close to or right at the narrower sections of the fiber bundle.

The data 21 may further comprise information relating to fiber orientation variations over the length of the fiber bundle. For example, when trying to simultaneously stimulate multiple fiber bundles or when trying to avoid stimulation of a nearby fiber bundle, it may be better to stimulate a differently oriented section of the fiber bundle instead of the narrowest section or the section closest to the stimulation electrodes.

Thus, in a preferred embodiment of the neurostimulation device 10 according to the invention, the calculation module 14 specifies a current distribution which results in an optimal balance between maximizing therapeutic effect and minimizing adverse side effects. This optimal current distribution takes into account diameters and orientations of different sections of one or more targeted fiber bundles and of one or more fiber bundles for which stimulation is preferably avoided.

Figure 2:
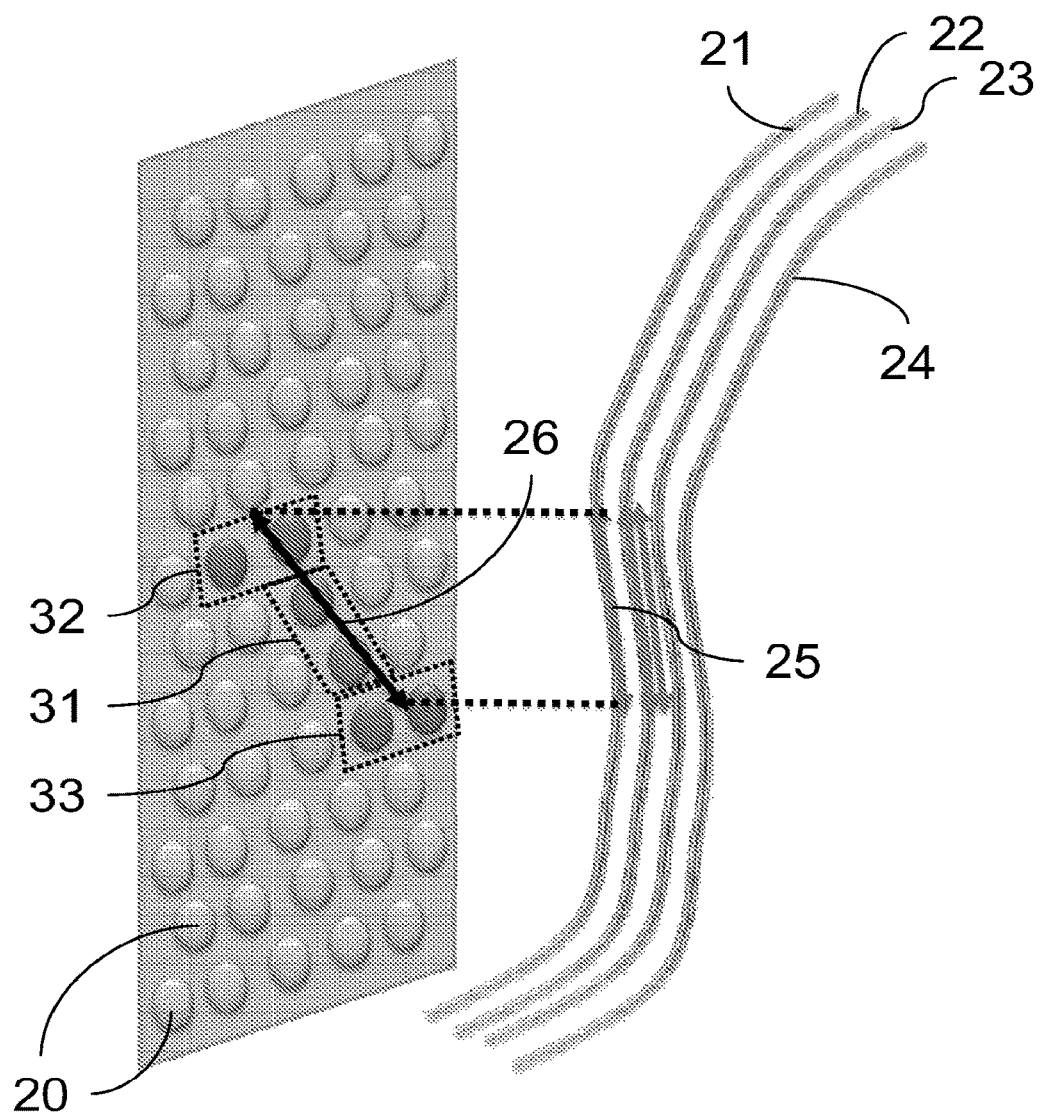
FIG. 2 illustrates how, according to the invention, a current distribution may be determined.

FIG. 2 illustrates how, according to the invention, a current distribution may be determined. The input data 21 describes positions and orientations of at least one fiber bundle 21 that is selected for stimulation. Additionally, the input data 21 may comprise information about nearby fiber bundles 22, 23, 24. In the following, we assume that the probe 12 is implanted close to fiber bundle 21 and that it is determined (either by the calculation module 14 or by an external planning system) that this fiber bundle 21 is to be stimulated at the section where the fiber orientation vector 25 is drawn.

The probe 12 comprises an array of stimulation electrodes 20. The calculation module 14 determines which of the available electrodes 20 are most suitable for providing the stimulation therapy. In order to minimize the strength of the electrical field to be generated, electrodes 31, 32, 33 close to the selected fiber section are selected. According to the invention, it is not enough to select a few electrodes 20 close to the selected fiber section, but it is also important to generate an electrical field with a properly oriented electrical field gradient.

The optimal current distribution leading to an optimal electric field gradient may, e.g., be determined as follows:

First, the fiber orientation vector 25 is projected onto the array of stimulation electrodes 20.

Then the calculation module 24 determines which currents should be applied to which electrodes 20 in order to obtain an electric field gradient that is parallel to the projected vector 26. In this example, a central group of electrodes 31 is selected.

A current value is assigned to the electrodes 31 in this central group.

At opposite sides of the central group of electrodes 31 and along the direction of the projected vector 26 a second and third group of electrodes 32, 33 are selected.

Current values for the second and third groups of electrodes 32, 33 are also determined. The current values for the second and third group 32, 33 have a polarity opposite to the polarity of the current value for the central group 31. As a result, the resulting electrical field gradient will be directed along the fiber orientation vector 25. The total current may be balanced by applying a current value to the central group of electrodes 31 which is, apart from the polarity, twice the current value applied to the second and third group of electrodes 32, 33.

It is to be noted that also other current distributions may lead to a suitably oriented electric filed gradient. In the provided exemplary situation, the fiber orientation vector 25 is a straight line and the electrodes 20 are provided on a flat surface. In a similar way, however, the calculation module 14 may calculate current distributions for stimulating curved fiber bundle sections. Also the array of stimulation electrodes does not have to be a flat surface.

Figure 3:
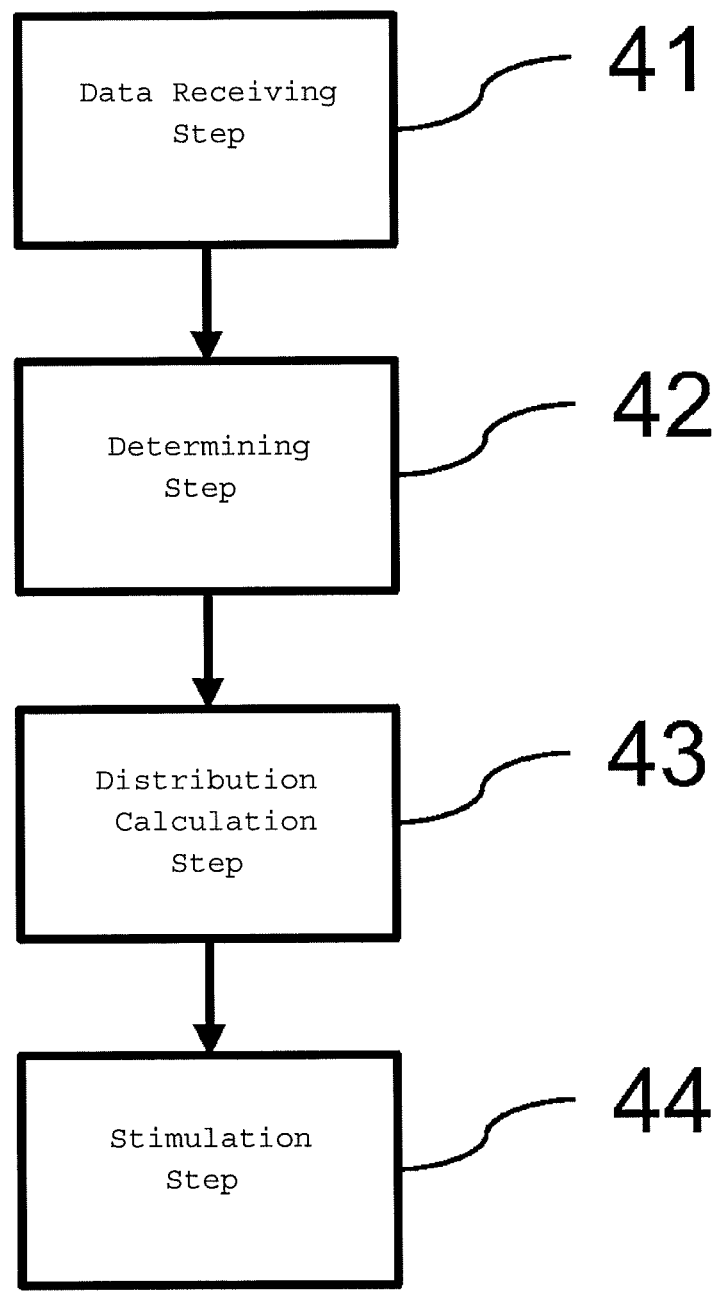
FIG. 3 shows a flow diagram of a method according to the invention.

FIG. 3 shows a flow diagram of a method according to the invention. The steps of this method may be performed by the distribution calculation module 14 of the neurostimulation device 10 of FIG. 1. The method starts with a data receiving step 41 for receiving the stimulation data 21 from the input 11 of the device 10. When the data 21 is sent to the device 10, the received data may directly be passed on to and processed by the distribution calculation module 14. Alternatively, the data 21 is temporarily stored in a memory for later use.

In orientation determining step 42, a preferred position and orientation for an electric field gradient to be generated by the array of stimulation electrodes 20 is determined. The position and orientation for the electric field gradient are determined based on the data received in the data receiving step 41. Above, with reference to FIG. 2, an exemplary method for doing so is described. In distribution calculation step 43 the current distribution leading to the determined position and orientation for the electric field gradient is calculated. The stimulation unit 13 may then apply the calculated current distributions to the respective stimulation electrodes 20 in stimulation step 44.

It will be appreciated that the invention also extends to computer programs, particularly computer programs on or in a carrier, adapted for putting the invention into practice. The program may be in the form of source code, object code, a code intermediate source and object code such as partially compiled form, or in any other form suitable for use in the implementation of the method according to the invention. It will also be appreciated that such a program may have many different architectural designs. For example, a program code implementing the functionality of the method or system according to the invention may be subdivided into one or more subroutines. Many different ways to distribute the functionality among these subroutines will be apparent to the skilled person. The subroutines may be stored together in one executable file to form a self-contained program. Such an executable file may comprise computer executable instructions, for example processor instructions and/or interpreter instructions (e.g. Java interpreter instructions). Alternatively, one or more or all of the subroutines may be stored in at least one external library file and linked with a main program either statically or dynamically, e.g. at run-time. The main program contains at least one call to at least one of the subroutines. Also, the subroutines may comprise function calls to each other. An embodiment relating to a computer program product comprises computer executable instructions corresponding to each of the processing steps of at least one of the methods set forth. These instructions may be subdivided into subroutines and/or be stored in one or more files that may be linked statically or dynamically. Another embodiment relating to a computer program product comprises computer executable instructions corresponding to each of the means of at least one of the systems and/or products set forth. These instructions may be subdivided into subroutines and/or be stored in one or more files that may be linked statically or dynamically.

The carrier of a computer program may be any entity or device capable of carrying the program. For example, the carrier may include a storage medium, such as a ROM, for example a CD ROM or a semiconductor ROM, or a magnetic recording medium, for example a floppy disc or hard disk. Further the carrier may be a transmissible carrier such as an electrical or optical signal, which may be conveyed via electrical or optical cable or by radio or other means. When the program is embodied in such a signal, the carrier may be constituted by such cable or other device or means. Alternatively, the carrier may be an integrated circuit in which the program is embedded, the integrated circuit being adapted for performing, or for use in the performance of, the relevant method.

It should be noted that the above-mentioned embodiments illustrate rather than limit the invention, and that those skilled in the art will be able to design many alternative embodiments without departing from the scope of the appended claims. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

I claim:

1. A neurostimulation device comprising:
   a neurostimulation probe with an array of stimulation electrodes;
   an input configured to receive stimulation data comprising information relating to a respective stimulation preferability of each respective nerve fiber bundle of a plurality of nerve fiber bundles and a respective orientation of each respective nerve fiber bundle of the plurality of nerve fiber bundles with respect to the array of stimulation electrodes, wherein the information relating to the stimulation preferability of each respective nerve fiber bundle indicates whether stimulation is to be delivered to the respective nerve fiber bundle;
   a distribution calculation module configured to:
      determine a position and an orientation of an electrical field gradient based on the stimulation data; and
      calculate a specified current distribution based on the determined position and determined orientation of the electrical field gradient; and
   a stimulation unit configured to, in accordance with the specified current distribution, provide currents to the array of stimulation electrodes.

2. The device of claim 1, wherein the determined position indicates a selected section of a nerve fiber bundle of the plurality of nerve fiber bundles.

3. The device of claim 2, wherein the specified current distribution is calculated to direct currents to electrodes close to the selected section of the nerve fiber bundle.

4. The device of claim 1, wherein the stimulation preferability of each respective nerve fiber bundle of the plurality of nerve fiber bundles is a binary value indicating that either stimulation is to be delivered or no stimulation is to be delivered to the respective nerve fiber bundle.

5. The device of claim 4, wherein the stimulation preferability of at least one of the plurality of stimulation bundles is to deliver stimulation to the nerve fiber bundle.

6. The device of claim 1, wherein the stimulation preferability of at least one nerve fiber bundle of the plurality of nerve fiber bundles is a value on a scale ranging from delivery of stimulation is highly preferable to absolutely no stimulation is to be delivered.

7. The device of claim 6, wherein the distribution calculation module is configured to, in response to the stimulation preferability of the at least one nerve fiber bundle being delivery of stimulation is highly preferable, determine a preferred orientation of the electric field gradient substantially parallel to the at least one nerve fiber bundle.

8. The device of claim 6, wherein the distribution calculation module is configured to, in response to the stimulation preferability of the at least one fiber bundle being delivery of stimulation is lowly preferable, determine a preferred orientation of the electric field gradient substantially perpendicular to the at least one fiber bundle.

9. The device of claim 1, wherein the distribution calculation module is configured to calculate the specified current distribution as a tripolar stimulation profile.

10. A method comprising:
    receiving stimulation data comprising information relating to a respective stimulation preferability of each respective fiber bundle of a plurality of nerve fiber bundles and a respective orientation of each respective nerve fiber bundle of the plurality of nerve fiber bundles with respect to an array of stimulation electrodes;
    determining, using a distribution calculation module, a position and a preferred orientation of an electrical field gradient based on the stimulation data;
    determining, using the distribution calculation module, a specified current distribution based on the position and orientation of the electrical field gradient; and
    providing current to the array of stimulation electrodes, via a stimulation unit, in accordance with the specified current distribution.

11. The method of claim 10, wherein the position indicates a selected section of a nerve fiber bundle of the plurality of nerve fiber bundles.

12. The method of claim 11, wherein providing current to the array of stimulation electrodes comprises directing currents to electrodes close to the selected section of the nerve fiber bundle based on the specified current distribution.

13. The method of claim 10, wherein the stimulation preferability of each respective nerve fiber bundle of the plurality of nerve fiber bundles is a binary value indicating either stimulation is to be delivered or no stimulation is to be delivered to the respective nerve fiber bundle.

14. The method of claim 13, wherein the stimulation preferability of at least one of the plurality of stimulation bundles is to deliver stimulation to the nerve fiber bundle.

15. The method of claim 10, wherein the stimulation preferability of at least one fiber bundle of the plurality of nerve fiber bundles is a value on a scale ranging from delivery of stimulation is highly preferable to absolutely no stimulation is to be delivered.

16. The method of claim 15, further comprising determining a preferred orientation of the electric field gradient substantially parallel to the at least one nerve fiber bundle in response to the stimulation preferability of the at least one nerve fiber bundle being delivery of stimulation is highly preferable.

17. The method of claim 15, further comprising determining a preferred orientation of substantially perpendicular to the at least one nerve fiber bundle in response to the stimulation preferability of the at least one nerve fiber bundle being delivery of stimulation is lowly preferable.

18. The method of claim 10, further comprising calculating the specified current distribution as a tripolar stimulation profile.

19. A neurostimulation device comprising:
  means for receiving stimulation data comprising information relating to a respective stimulation preferability of each respective fiber bundle of a plurality of nerve fiber bundles and a respective orientation of each respective nerve fiber bundle of the plurality of nerve fiber bundles with respect to an array of stimulation electrodes;
  means for determining a position and a preferred orientation of an electrical field gradient based on the stimulation data;
  means for determining a specified current distribution based on the position and orientation of the electrical field gradient; and
  means for providing current to the array of stimulation electrodes, in accordance with the specified current distribution.

20. The neurostimulation device of claim 19, wherein the stimulation preferability of each respective nerve fiber bundle of the plurality of nerve fiber bundles is a binary value indicating that either stimulation is to be delivered or no stimulation is to be delivered to the respective nerve fiber bundle.

* * * * *